(12) United States Patent
Kolluri et al.

(10) Patent No.: US 8,047,998 B2
(45) Date of Patent: Nov. 1, 2011

(54) NON-INVASIVE BLOOD PRESSURE DETERMINATION METHOD

(75) Inventors: Sai Kolluri, Tampa, FL (US); Lawrence T. Hersh, Tampa, FL (US); Bruce A. Friedman, Tampa, FL (US)

(73) Assignee: General Electric Company, Schenectady, NY (US)

( * ) Notice: Subject to any disclaimer, the term of this patent is extended or adjusted under 35 U.S.C. 154(b) by 1232 days.

(21) Appl. No.: 11/736,276

(22) Filed: Apr. 17, 2007

(65) Prior Publication Data

US 2008/0262362 A1     Oct. 23, 2008

(51) Int. Cl.
*A61B 5/022* (2006.01)
(52) U.S. Cl. .................. 600/494; 600/485; 600/490
(58) Field of Classification Search .............. 600/494, 600/485, 486, 487, 490, 496, 493, 492, 491, 600/488
See application file for complete search history.

(56) References Cited

U.S. PATENT DOCUMENTS 6,599,251 B2 *   7/2003   Chen et al. ............... 600/485
6,648,828 B2    11/2003   Friedman et al.

FOREIGN PATENT DOCUMENTS

| EP | 0 443 267 | 8/1991 |
|----|-----------|--------|
| WO | WO 00/47110 | 8/2000 |

OTHER PUBLICATIONS

G. Geršak, Valentin Baatagelj, and J. Drnovšek, "Oscillometric Virtual Instrument for Blood Pressure Measurement.", XVIII IMEKO World Congress, Sep. 17-22, 2006, pp. 1-2.*
Jya Foo, CS Lim, SJ Wilson, GR Williams, M-A Harris, and DM Cooper, "Pulse transit time ratio as a potential marker for paediatric crural and brachial blood pressure index.", published online Feb. 8, 2007, Nature Publishing Group, Journal of Human Hypertension (2007) 21, p. 1.*

* cited by examiner

*Primary Examiner* — Charles A Marmor, II
*Assistant Examiner* — Tho Tran
(74) *Attorney, Agent, or Firm* — Andrus, Sceales, Starke & Sawall, LLP

(57) ABSTRACT

A method for estimating systolic and diastolic pressure is disclosed herein. The method includes obtaining a predetermined type of blood pressure data from a patient, and providing previously acquired blood pressure data obtained from a plurality of different subjects. The method also includes implementing the previously acquired blood pressure data to select systolic and diastolic amplitude ratios that most closely correlate with the predetermined type of blood pressure data obtained from the patient. The selected systolic and diastolic amplitude ratios are adapted to compensate for the effects of arterial compliance. The method also includes implementing the selected systolic and diastolic amplitude ratios to generate a systolic and diastolic blood pressure estimates.

19 Claims, 8 Drawing Sheets

NON-INVASIVE BLOOD PRESSURE DETERMINATION METHOD

FIELD OF THE INVENTION

This disclosure relates generally to a method for non-invasively determining a patient's blood pressure.

BACKGROUND OF THE INVENTION

An accurate and reliable technique for continuously measuring blood pressure involves inserting a saline filled catheter through the patient's vascular system to the point at which it is desired to perform the measurements. The catheter is connected to a pressure sensor, which measures the pressure in the vessel. An alternative method uses a catheter with a pressure sensor at the tip that directly senses the blood pressure. Procedures such as these are commonly referred to as "invasive procedures" because they involve making an incision through the patient's skin and inserting the catheter into a blood vessel. A problem with invasive procedures is that they can cause patient discomfort and increase the risk of complications such as infection.

Non-invasive blood pressure (NIBP) algorithms typically inflate a pressure cuff above the patient's systolic pressure and measure oscillations under the cuff as the cuff is deflated either in steps or continuously. The resulting oscillometric envelope is used to determine the patients' blood pressure. The cuff pressure corresponding to the maximum oscillation amplitude is typically taken as the mean arterial pressure (MAP). Systolic and Diastolic pressures are computed using a fixed ratio of the maximum oscillation amplitude. Some NIBP monitors also use the shape of the oscillometric envelope to compute the Systolic and Diastolic pressures. The problem with conventional NIBP techniques is that they do not compensate for arterial compliance changes and are therefore imprecise.

BRIEF DESCRIPTION OF THE INVENTION

The above-mentioned shortcomings, disadvantages and problems are addressed herein which will be understood by reading and understanding the following specification.

In an embodiment, a method for estimating systolic blood pressure and diastolic blood pressure includes obtaining a predetermined type of blood pressure data from a patient, and providing previously acquired blood pressure data obtained from a plurality of different subjects. The previously acquired blood pressure data is adapted to convey the manner in which a systolic amplitude ratio and a diastolic amplitude ratio vary with respect to the predetermined type of blood pressure pulse data obtained from the patient. The method also includes implementing the previously acquired blood pressure data to select a systolic amplitude ratio and a diastolic amplitude ratio that most closely correlate with the predetermined type of blood pressure data obtained from the patient. The selected systolic amplitude ratio and diastolic amplitude ratio are adapted to compensate for the effects of arterial compliance. The method also includes implementing the selected systolic amplitude ratio and the selected diastolic amplitude ratio to generate a systolic blood pressure estimate and a diastolic blood pressure estimate.

In another embodiment, a method for estimating systolic blood pressure and diastolic blood pressure includes providing a non-invasive blood pressure monitor having a cuff configured to apply a selectable pressure level to a patient. The method also includes estimating a first pulse transit time at a first cuff pressure level, and a second pulse transit time at a second cuff pressure level. The method also includes calculating a pulse transit time ratio, which is defined as the first pulse transit time divided by the second pulse transit time. The method also includes providing blood pressure data adapted to correlate a plurality of pulse transit time ratios with a corresponding plurality of systolic amplitude ratios and diastolic amplitude ratios. The method also includes selecting one of the systolic amplitude ratios and one of the diastolic amplitude ratios that most closely correlate with the calculated pulse transit time ratio. The selected systolic and diastolic amplitude ratios are adapted to compensate for the effects of arterial compliance. The method also includes implementing the selected systolic and diastolic amplitude ratios to generate a systolic blood pressure estimate and a diastolic blood pressure estimate.

In yet another embodiment, a method for estimating systolic blood pressure and diastolic blood pressure includes estimating a pulse wave velocity of a blood pressure pulse being transmitted through a patient. The method also includes providing blood pressure data adapted to correlate a plurality of pulse wave velocity values with a plurality of systolic amplitude ratios and a plurality of diastolic amplitude ratios. The method also includes selecting one of the plurality of systolic amplitude ratios and one of the plurality of diastolic amplitude ratios that are most closely correlated with the estimated pulse wave velocity. The selected systolic and diastolic amplitude ratios are adapted to compensate for the effects of arterial compliance. The method also includes implementing the selected systolic and diastolic amplitude ratios to generate a systolic blood pressure estimate and a diastolic blood pressure estimate.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
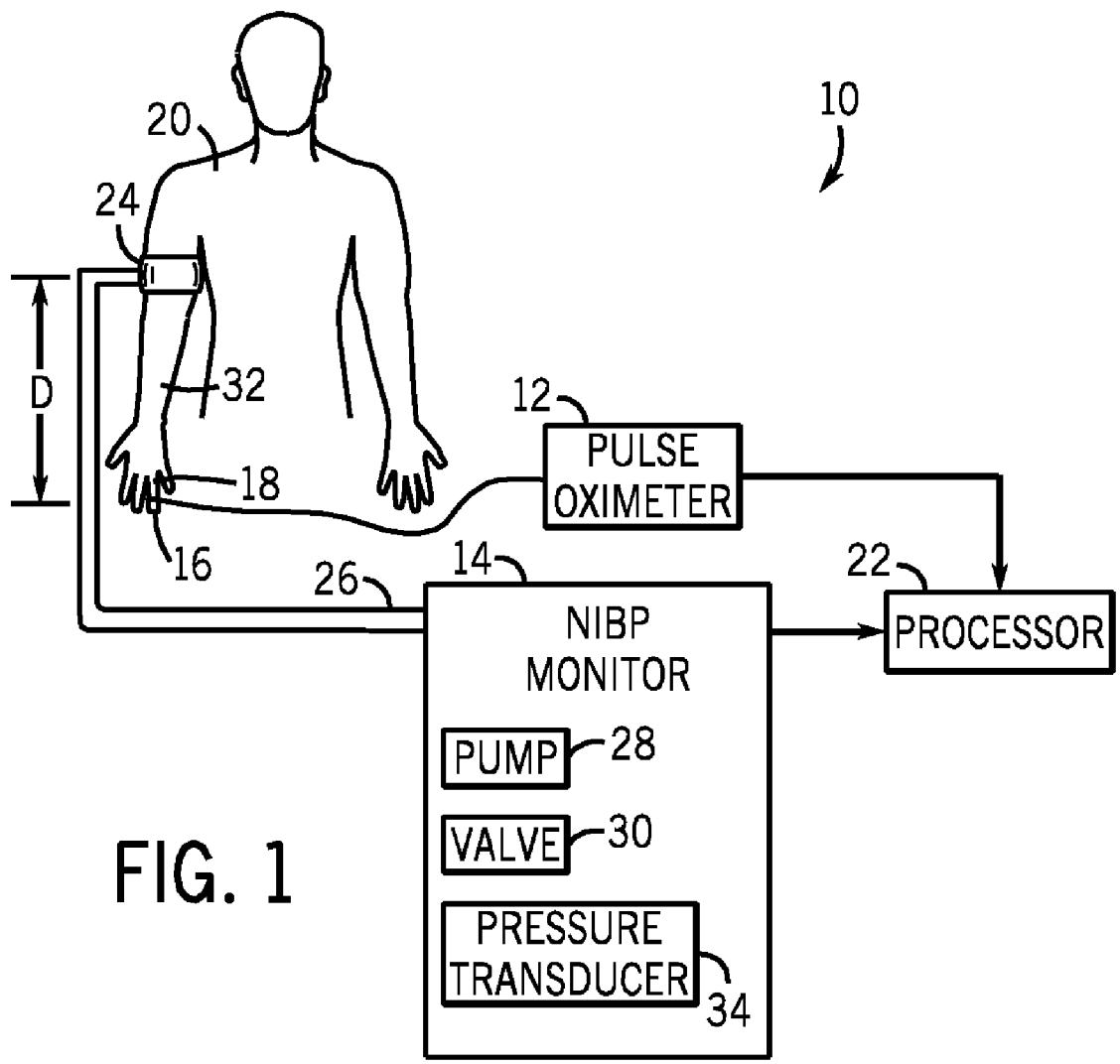
FIG. 1 is a schematic diagram of a patient monitoring system in accordance with an embodiment.

Referring to FIG. 1, a patient monitoring system 10 is shown in accordance with an embodiment. The patient monitoring system 10 includes a pulse oximeter 12 and a non-invasive blood pressure (NIBP) monitor 14. The pulse oximeter 12 is connected to a probe 16 that is attachable to a finger 18 of a patient 20. The pulse oximeter 12 is operable to sense or identify volume pulses referred to hereinafter as SpO2 pulses at the patient's finger 18, and to thereafter transmit data pertaining to the SpO2 pulses to a processor 22.

The NIBP monitor 14 is connected to an inflatable cuff 24 via a flexible tube 26. The NIBP monitor 14 includes a pump 28 adapted to inflate the cuff 24, and one or more valves 30 adapted to deflate the cuff 24. In the embodiment depicted, the inflatable cuff 24 is wrapped around the patient's upper arm 32, however other locations (e.g., forearm) and other limbs could also be used. The NIBP monitor 14 includes a pressure transducer 34 operable to sense or identify pressure pulses referred to hereinafter as NIBP pulses at the portion of the patient's arm 32 to which the cuff 24 is attached. Thereafter, the NIBP monitor 14 can transmit data pertaining to the NIBP pulses to the processor 22.

Figure 2:
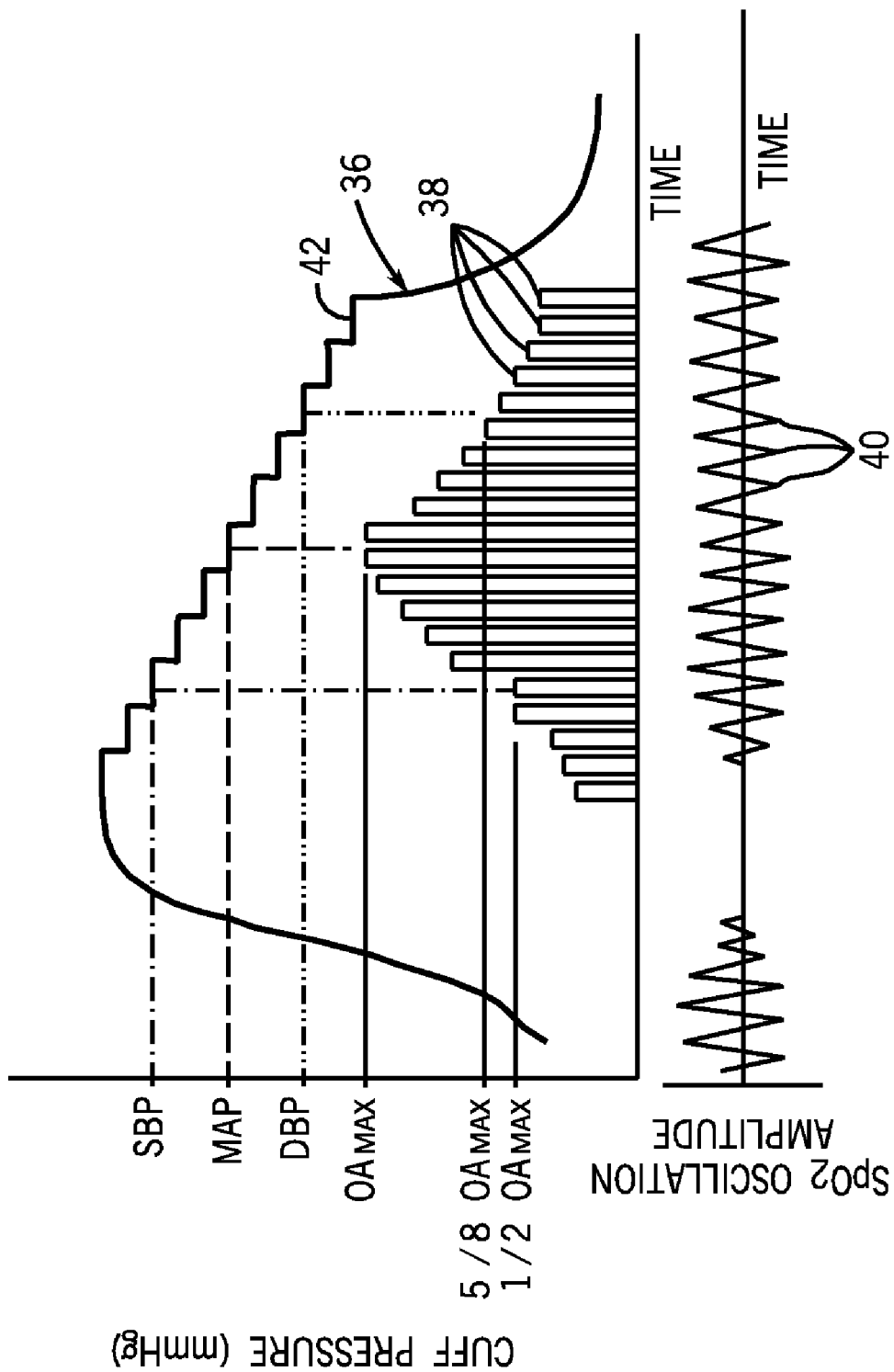
FIG. 2 is a graph of cuff pressure versus time illustrating a method for estimating blood pressure using a non-invasive blood pressure monitoring system.

The NIBP monitor 14 is configured to measure mean arterial pressure (MAP), systolic blood pressure (SBP), and diastolic blood pressure (DBP) in a known manner. With reference to FIGS. 1 and 2, a process of measuring MAP, SBP and DBP will be described for exemplary purposes in accordance with one embodiment.

The exemplary process of measuring MAP, SBP and/or DBP is performed by increasing and decreasing the pressure of the cuff 24 in the manner illustrated by the cuff pressure curve 36 of FIG. 2, and generally simultaneously measuring a series of NIBP pulses 38. This process is initiated by implementing the pump 28 to inflate the cuff 24 and thereby increase cuff 24 pressure to a supra-systolic pressure level. As is known in the art, at supra-systolic cuff pressure blood is completely occluded or obstructed from flowing through the artery under the cuff 24, systolic pressure is the cuff pressure level at which blood just begins flowing through the artery under the cuff 24, and diastolic pressure is the cuff pressure level at which blood flow through the artery under the cuff 24 is unobstructed. After cuff 24 pressure is increased to a supra-systolic pressure level, the cuff 24 is deflated (via valve 30) in a controlled manner adapted to produce a series of decreasing pressure level steps. It should be appreciated that while the exemplary embodiment has been described and depicted as including a stepwise cuff pressure reduction, other embodiments may alternatively implement a generally continuous cuff pressure reduction.

After the cuff 24 reaches systolic pressure, the pressure level measured by the pressure transducer 34 oscillates due to the force exerted on the cuff 24 by the entry of blood into the artery under the cuff 24. The term "oscillation" refers to a measurable pressure level oscillation produced by this change in volume. Two consecutive oscillations are generally measured at each cuff pressure level step. As shown in FIG. 2, MAP is identifiable as the cuff pressure level at which oscillation amplitude is maximum ($OA_{max}$). SBP is identifiable as the cuff pressure level at which oscillation amplitude is approximately equal to ($0.5*(OA_{max})$), and DBP is identifiable as the cuff pressure level at which oscillation amplitude is approximately equal to ($0.625*(OA_{max})$). A plurality of SpO2 pulses 40 are also shown in FIG. 2 to illustrate typical SpO2 data acquired during the previously described cuff inflation/deflation sequence.

The processor 22 is operable to calculate pulse transit time (PTT) in response to data from the pulse oximeter 12 and the NIBP monitor 14. For purposes of this disclosure, PTT is defined as the time required for a given pressure pulse to travel from one reference point (e.g., the patient's arm 32) to another reference point (e.g., the patient's finger 18). It will be understood by those skilled in the art that a pressure pulse is accompanied by a volume pulse, which is what is measured by the NIBP cuff 24 and the probe 16. As an example, if the probe 16 and cuff 24 are attached to the same limb, PTT can be calculated by measuring the time interval between a NIBP pulse and an immediately subsequent SpO2 pulse. PTT can be measured, for example, as the "foot-to-foot delay", the "peak-to-peak delay", or the delay between maximum slope points. The "foot-to-foot delay" refers to the time interval measured between the foot of a NIBP pulse and the foot of an immediately subsequent SpO2 pulse. Similarly, the "peak-to-peak delay" refers to the time interval measured between the peak of a NIBP pulse and the peak of an immediately subsequent SpO2 pulse.

Figure 3:
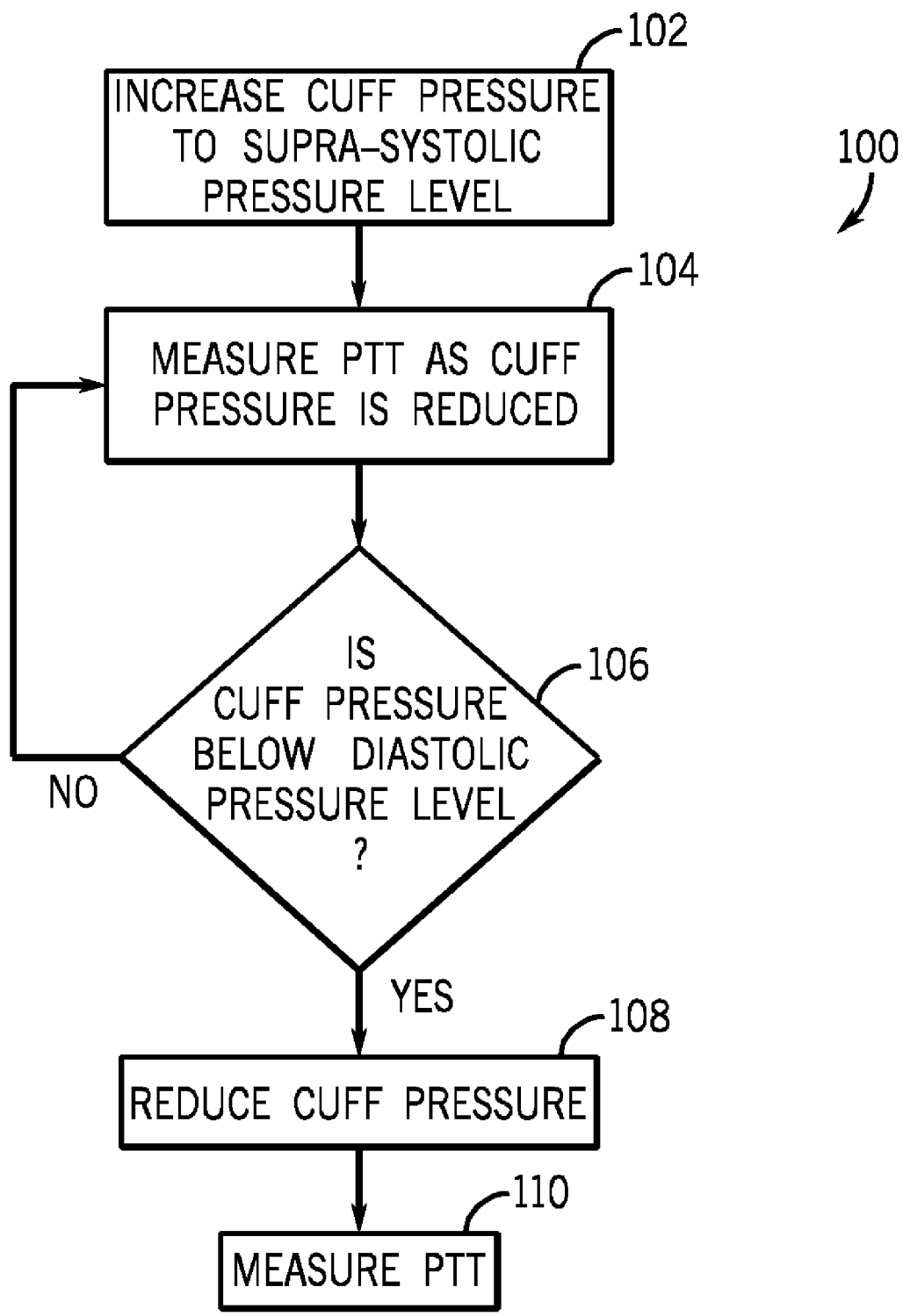
FIG. 3 is a block diagram illustrating a method in accordance with an embodiment.

FIG. 3 is flow chart illustrating a method 100 that is also referred to hereinafter as the algorithm 100. The individual blocks of the flow chart represent steps that may be performed in accordance with the method 100. Unless otherwise specified, the steps 102-110 need not be performed in the order shown.

Referring now to FIGS. 1 and 3, at step 102, cuff 24 pressure is increased to a supra-systolic pressure level. At step 104, the cuff 24 pressure is reduced in a controlled manner which may include, for example, a stepwise pressure reduction or a generally continuous pressure reduction. Also at step 104, while cuff 24 pressure is being reduced, the processor 22 measures PTT. As previously described, PTT can be measured by measuring the time interval between each NIBP pulse and the immediately subsequent SpO2 pulse.

At step 106, the algorithm 100 determines whether the current cuff 24 pressure value is below diastolic pressure. This determination can be made by comparing a current cuff 24 pressure value measured by the pressure transducer 34 with the calculated DBP value. The DBP value can be calculated using a baseline amplitude ratio that is not adjusted for pulse transit time such as, for example, the previously described DPB amplitude ratio of 0.625, or can alternatively be calculated in any other known manner. If, at step 106, the current cuff 24 pressure is not below diastolic pressure, the algorithm 100 returns to step 104. If, at step 106, the current cuff 24 pressure is below diastolic pressure, the algorithm 100 proceeds to step 108.

At step 108, cuff 24 pressure is reduced. If cuff 24 pressure is being reduced in a stepwise manner, the cuff 24 pressure is further reduced by one step. If cuff 24 pressure is being reduced in a generally continuous manner, the cuff 24 pressure is further reduced in a continuous manner by 10 mm Hg. At step 110, the processor 22 measures PTT. The PTT measurement of step 110 is taken at a sub-diastolic pressure level.

Figure 4:
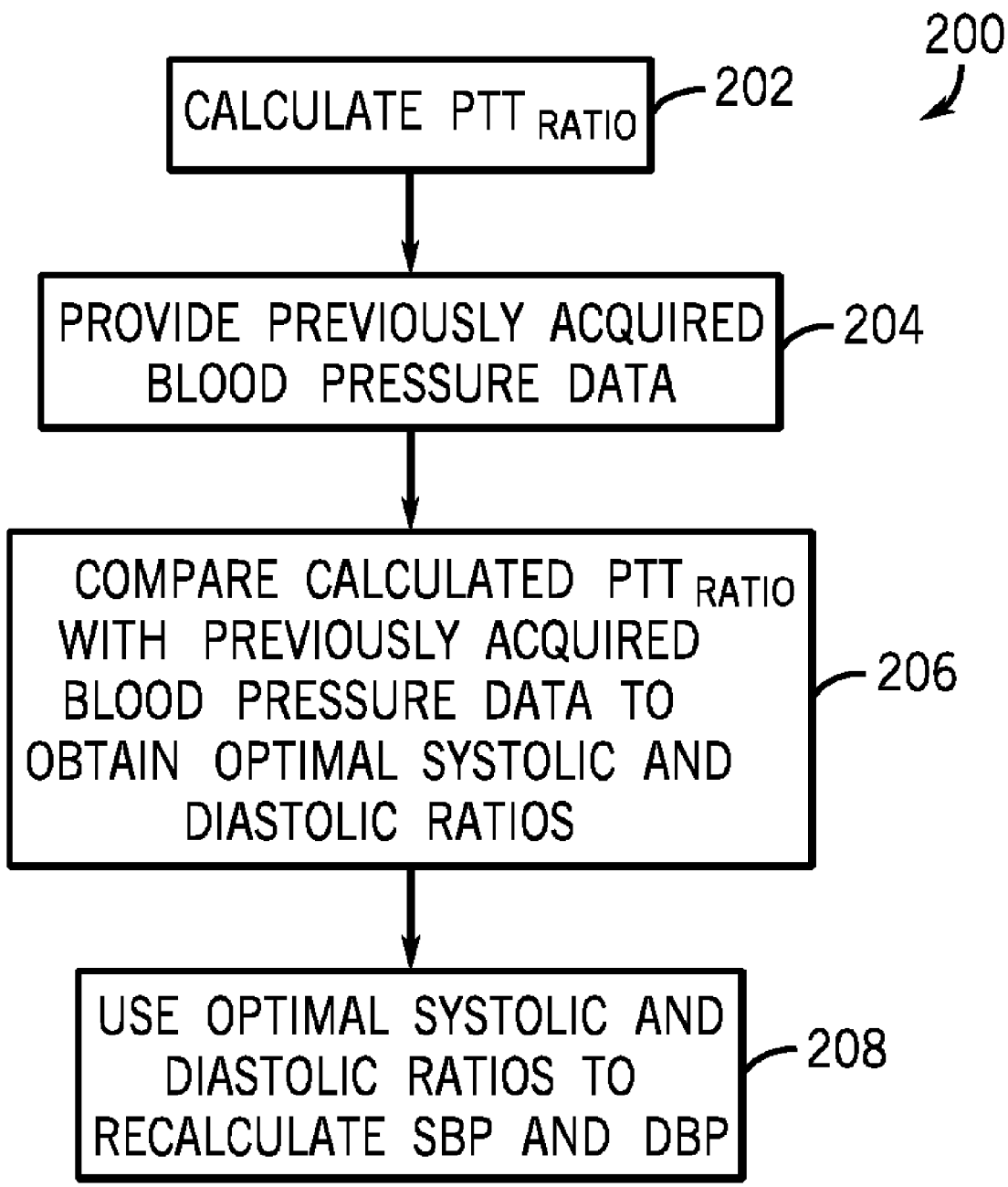
FIG. 4 is a block diagram illustrating a method in accordance with an embodiment.

Referring to FIG. 4, a flow chart illustrates a method 200 adapted for use in combination with the method 100 (shown in FIG. 3) to precisely estimate SBP and DBP. The method 200 may also be referred to hereinafter as the algorithm 200. The individual blocks of the flow chart represent steps that may be performed in accordance with the method 200. Unless otherwise specified, the steps 202-208 need not be performed in the order shown.

At step 202, $PTT_{ratio}$ is calculated according to the equation $PTT_{ratio}=(PTT_{MAP}/PTT_{subdias})$. The variable $PTT_{MAP}$ represents the pulse transit time measured at the mean arterial pressure level, and is acquired by the processor 22 (shown in FIG. 1) at step 104 of the algorithm 100 (shown in FIG. 3) in the manner previously described. The variable $PTT_{subdias}$ represents the pulse transit time measured at a sub-diastolic pressure level, and is acquired by the processor 22 at step 110 of the algorithm 100 in the manner previously described.

At step 204, previously acquired blood pressure data is provided. The previously acquired blood pressure data generally represents multiple blood pressure measurements taken in a known manner (e.g., via intra-arterial, oscillometric and/or auscultatory procedures) from a plurality of different individuals. The previously acquired blood pressure data is preferably provided in a format adapted to correlate $PTT_{ratio}$ with systolic and diastolic amplitude ratios. As an example, the previously acquired blood pressure data may be provided in the form of a graph as depicted in FIG. 4a, however it should be appreciated that the data may alternatively be provided in any known format including, for example, a look-up table, a spreadsheet, an equation correlating $PTT_{ratio}$ with the amplitude ratios or a database.

Figure 4A:
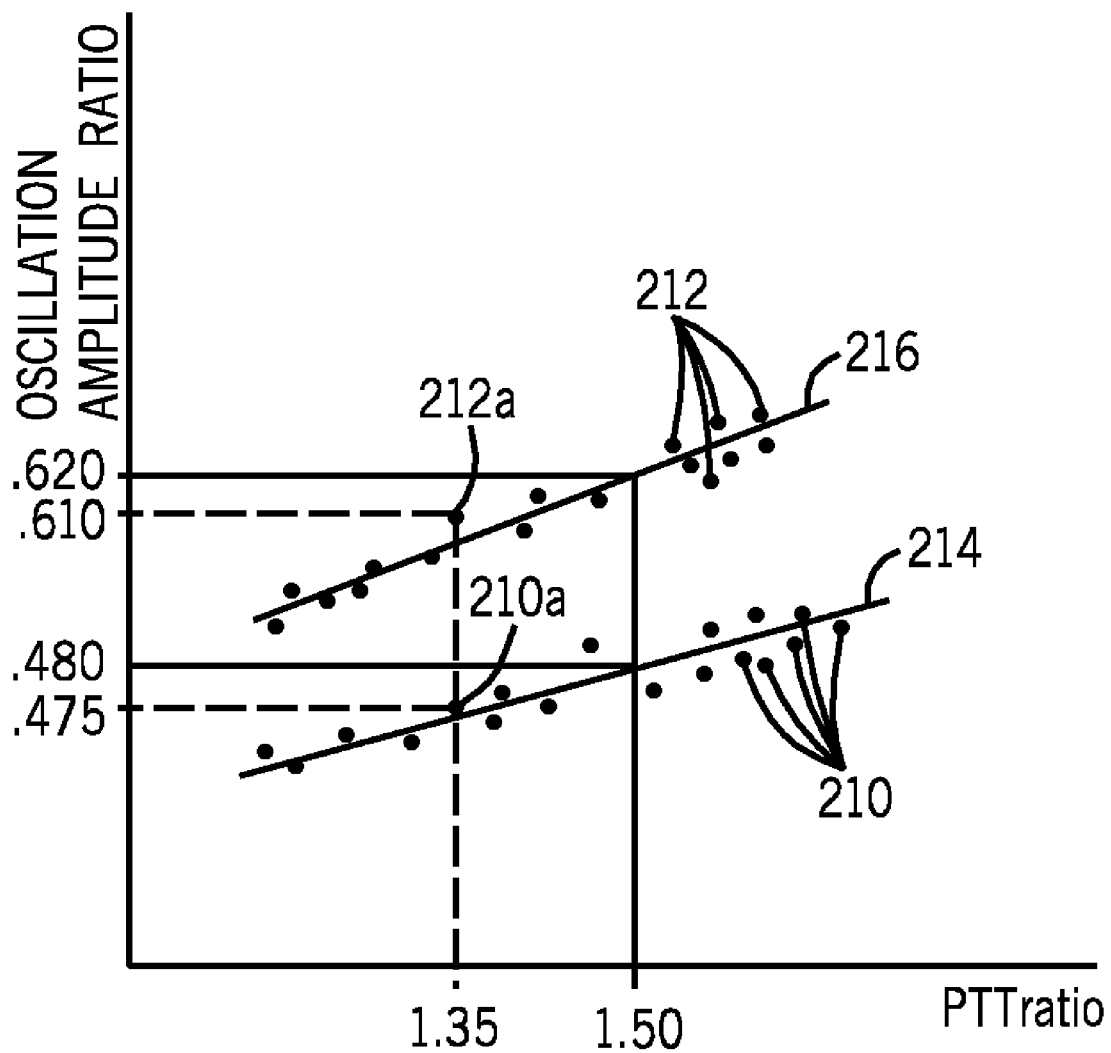
FIG. 4a is a graph of oscillation amplitude versus $PTT_{ratio}$.

Referring to FIG. 4a, a graph of oscillation amplitude versus $PTT_{ratio}$ is shown to illustrate a method for compiling previously acquired blood pressure data in accordance with step 204 of the algorithm 200 (shown in FIG. 4). $PTT_{ratio}$ may be calculated, for example, in accordance with the previously provided equation $PTT_{ratio}=(PTT_{MAP}/PTT_{subdias})$. The graph of FIG. 4a can be generated by calculating SBP amplitude ratio, DBP amplitude ratio and $PTT_{ratio}$ values for each of the previously acquired blood pressure measurements. Thereafter, a SBP data point 210 having (X, Y) coordinate values of ($PTT_{ratio}$, SBP amplitude ratio), and a DBP data point 212 having (X, Y) coordinate values of ($PTT_{ratio}$, DBP amplitude ratio) are plotted for each previously acquired blood pressure measurement. An SBP best-fit line 214 is calculated for the SBP data points 210 and a DBP best-fit line 216 is calculated for the DBP data points 212. The process of calculating a "best-fit line" is well known mathematical process and therefore will not be described in detail. While a linear fit is shown in FIG. 4a, the data might also be fitted to a polynomial, exponential or other curvilinear function.

A non-limiting example will now be provided to better illustrate the previously described method for generating the graph of FIG. 4a. For purposes of this example, assume that the previously acquired blood pressure of a single test subject was intra-arterially measured, and that this test subject was determined to have a PTT of 95 milliseconds at MAP, a PTT of 70 milliseconds at a sub-diastolic pressure level, a systolic oscillation amplitude ratio of 0.475, and a diastolic oscillation amplitude ratio of 0.610. The "systolic oscillation amplitude ratio" refers to the test subject's oscillation amplitude at SBP divided by their oscillation amplitude at MAP, and the "diastolic oscillation amplitude ratio" refers to the patient's oscillation amplitude at DBP divided by their oscillation amplitude at MAP. For the exemplary embodiment, $PTT_{ratio}$ is calculated as $(PTT_{MAP}/PTT_{subdias})$ or (95/70)=1.35. Accordingly, the exemplary SBP data point 210a having (X, Y) coordinate values of (1.35, 0.475), and the exemplary DBP data point 212a having (X, Y) coordinate values of (1.35, 0.610) are plotted as shown in FIG. 4a. After plotting SBP data points 210 and DBP data points 212 for each of a plurality of different test subjects in the manner previously described, the SBP best-fit line 214 is calculated for the SBP data points 210 and the DBP best-fit line 216 is calculated for the DBP data points 212.

Referring to FIG. 4, at step 206 the $PTT_{ratio}$ value calculated at step 202 is compared with previously acquired blood pressure data of step 204 in order to obtain optimal systolic and diastolic ratios. As a non-limiting example, assume that the $PTT_{ratio}$ calculated at step 202 is equal to 1.50, and that the previously acquired blood pressure data provided at step 204 is represented by the graph of FIG. 4a. For purposes of this non-limiting example, the optimal systolic ratio is 0.480 which is the Y-axis value corresponding to the point of intersection between the X-axis $PTT_{ratio}$ value (i.e., 1.50) and the SBP best-fit line 214. Similarly, the optimal diastolic ratio is 0.620 which is the Y-axis value corresponding to the point of intersection between the X-axis $PTT_{ratio}$ value (i.e., 1.50) and the DBP best-fit line 216. It should be appreciated that, unlike conventional fixed systolic and diastolic amplitude ratios, the previously described optimal systolic and diastolic amplitude ratios are variable to compensate for the effects of arterial compliance.

Referring again to FIG. 4, at step 208 the optimal systolic and diastolic ratios that were obtained at step 206 are used to recalculate SBP and DBP. The previously calculated optimal systolic amplitude ratio value 0.480 and optimal diastolic amplitude ratio value 0.620 will again be used for illustrative purposes. Referring to FIG. 2 and according to the illustrative embodiment, SBP can be recalculated as the cuff pressure level at which NIBP oscillation amplitude is approximately equal to $(0.480*(OA_{max}))$, and DBP can be recalculated as the cuff pressure level value at which NIBP oscillation amplitude is approximately equal to $(0.620*(OA_{max}))$. The recalculated SBP and DBP values are generally more accurate than conventional SBP/DBP estimates because the recalculated values are based on optimal systolic and diastolic amplitude ratios selected to compensate for the effects of arterial compliance.

Figure 5:
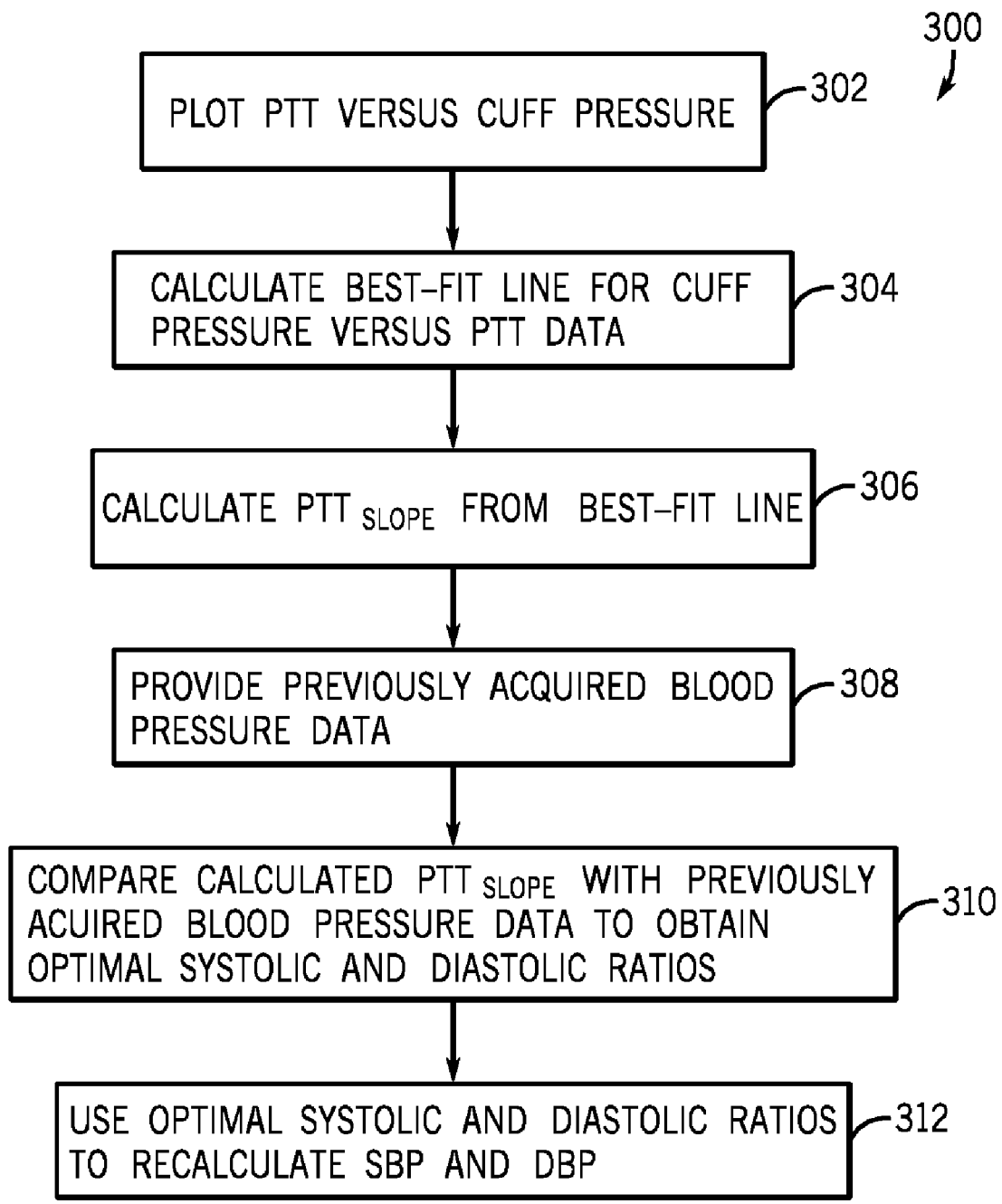
FIG. 5 is a block diagram illustrating a method in accordance with an embodiment.

Referring to FIG. 5, a flow chart illustrates a method 300 adapted for use in combination with the method 100 (shown in FIG. 3) to precisely estimate SBP and DBP. The method 300 may also be referred to hereinafter as the algorithm 300. The individual blocks of the flow chart represent steps that may be performed in accordance with the method 300. Unless otherwise specified, the steps 302-312 need not be performed in the order shown.

Figure 5A:
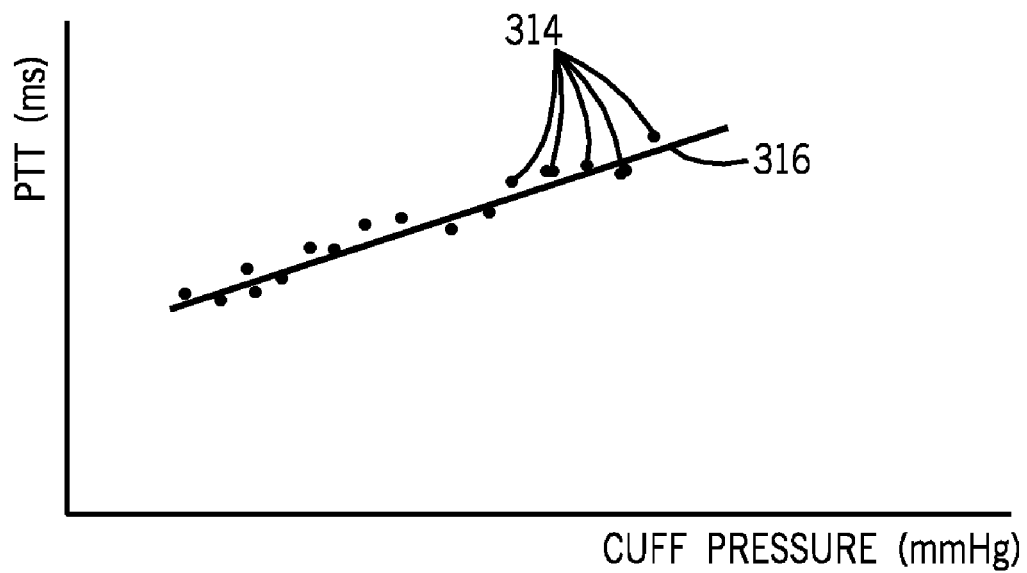
FIG. 5a is a graph of PTT versus cuff pressure.

At step 302, PTT versus cuff pressure data points 314 are plotted as shown in FIG. 5a. The data points 314 represent the pulse transit time measured during the process of reducing cuff pressure level, and are obtained from steps 104 and 110 of the algorithm 100 (shown in FIG. 3). At step 304, a best-fit line 316 (shown in FIG. 5a) is calculated for the data points 314. At step 306, $PTT_{slope}$ is calculated as the slope of the best-fit line 316.

At step 308, previously acquired blood pressure data is provided. The previously acquired blood pressure data generally represents multiple blood pressure measurements taken in a known manner (e.g., via intra-arterial, oscillometric and/or auscultatory procedures) from a plurality of different individuals. The previously acquired blood pressure data is preferably provided in a format adapted to correlate $PTT_{slope}$ with systolic and diastolic amplitude ratios. As an example, the previously acquired blood pressure data may be provided in the form of a graph as depicted in FIG. 5b, however it should be appreciated that the data may alternatively be provided in any known format including, for example, a look-up table, a spreadsheet, an equation correlating the $PTT_{slope}$ with the amplitude ratios or a database.

Figure 5B:
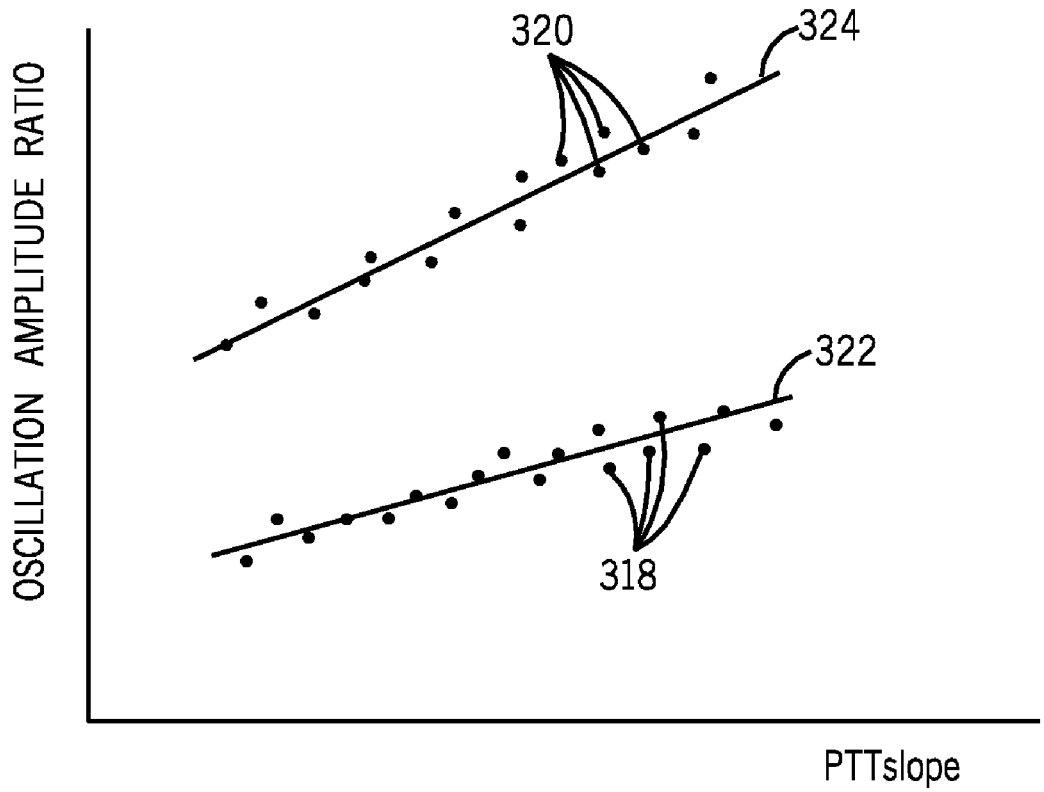
FIG. 5b is a graph of oscillation amplitude versus $PTT_{slope}$.

Referring to FIG. 5b, a graph of oscillation amplitude versus $PTT_{slope}$ is shown to illustrate a method for compiling previously acquired blood pressure data in accordance with step 308 of the algorithm 300 (shown in FIG. 5). The graph of FIG. 5b can be generated by calculating SBP amplitude ratio, DBP amplitude ratio and $PTT_{slope}$ values for each of the previously acquired blood pressure measurements. Thereafter, a SBP data point 318 having (X, Y) coordinate values of (PTT$_{slope}$, SBP amplitude ratio), and a DBP data point 320 having (X, Y) coordinate values of (PTT$_{slope}$, DBP amplitude ratio) are plotted for each previously acquired blood pressure measurement. An SBP best-fit line 322 is calculated for the SBP data points 318 and a DBP best-fit line 324 is calculated for the DBP data points 320. While a linear fit is shown in FIG. 5b, the data might also be fitted to a polynomial, exponential or other curvilinear function.

Referring to FIG. 5, at step 310 the PTT$_{slope}$ value calculated at step 306 is compared with previously acquired blood pressure data of step 308 in order to obtain optimal systolic and diastolic ratios. According to the embodiment wherein the blood pressure data is complied in the form of a graph, the optimal systolic ratio is the Y-axis value corresponding to the point of intersection between the X-axis PTT$_{slope}$ value (obtained at step 306) and the SBP best-fit line 322 (shown in FIG. 5b). Similarly, the optimal diastolic ratio is the Y-axis value corresponding to the point of intersection between the X-axis PTT$_{slope}$ value (obtained at step 306) and the DBP best-fit line 324 (shown in FIG. 5b). At step 312 the optimal systolic and diastolic ratios are used to recalculate SBP and DBP in a manner similar to that previously described with respect to step 208 of the algorithm 200 (shown in FIG. 4). The recalculated SBP and DBP values are generally more accurate than conventional SBP/DBP estimates because the recalculated values are based on optimal systolic and diastolic amplitude ratios selected to compensate for the effects of arterial compliance.

Figure 6:
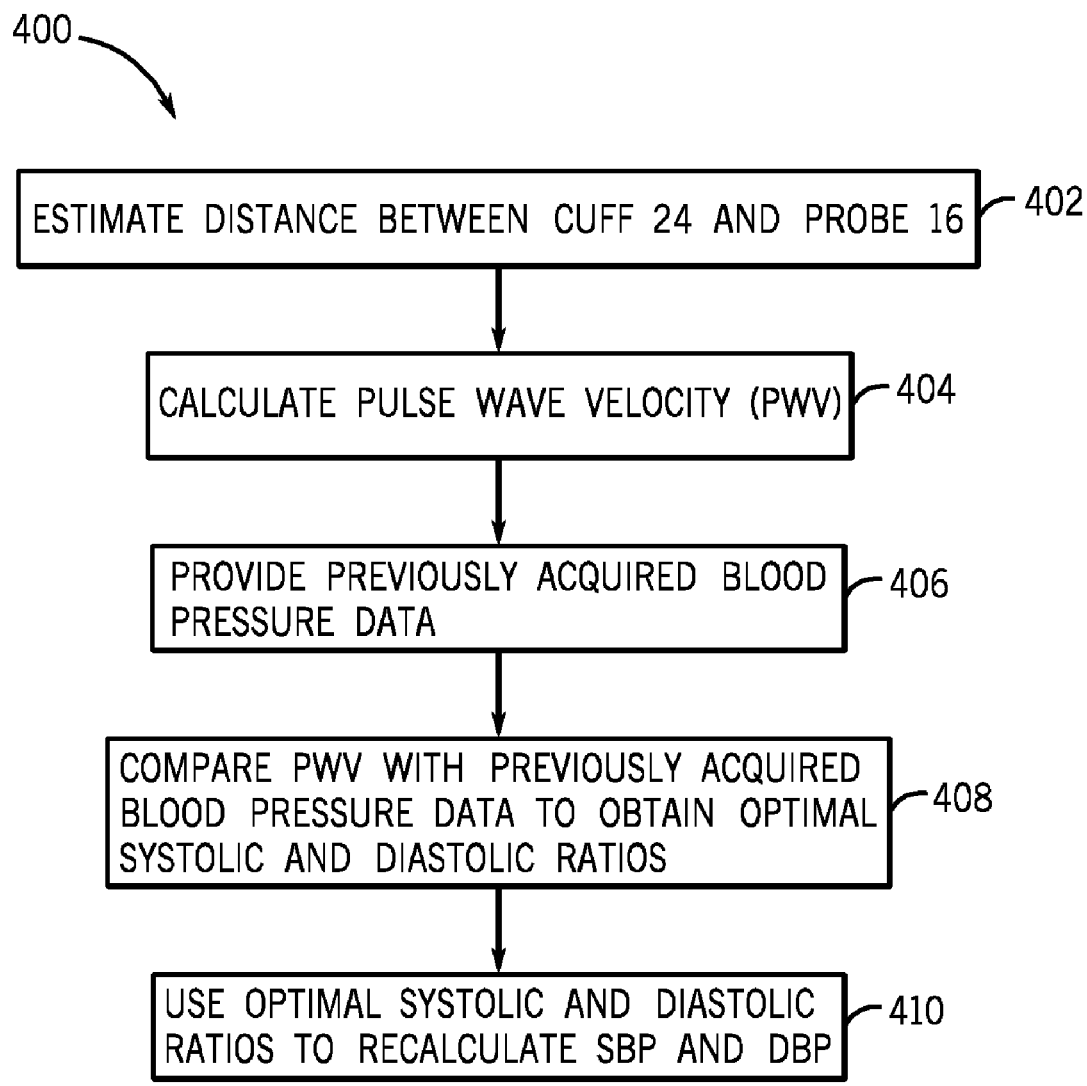
FIG. 6 is a block diagram illustrating a method in accordance with an embodiment.

Referring to FIG. 6, a flow chart illustrates a method 400 adapted for use in combination with the method 100 (shown in FIG. 3) to precisely estimate SBP and DBP. The method 400 may also be referred to hereinafter as the algorithm 400. The individual blocks of the flow chart represent steps that may be performed in accordance with the method 400. Unless otherwise specified, the steps 402-410 need not be performed in the order shown.

At step 402, the distance D (shown in FIG. 1) between the cuff 24 and the probe 16 is estimated. The distance D can be estimated in any known manner such as, for example, by physically measuring this distance along the arm 32 of the patient 20 (shown in FIG. 1). At step 404, pulse wave velocity (PWV) is calculated according to, the equation PWV=D/PTT. PTT values for this calculation can be obtained at steps 104 and/or 108 of the algorithm 100 (shown in FIG. 3).

At step 406, previously acquired blood pressure data is provided. The previously acquired blood pressure data generally represents multiple blood pressure measurements taken in a known manner (e.g., via intra-arterial, oscillometric and/or auscultatory procedures) from a plurality of different individuals. The previously acquired blood pressure data is preferably provided in a format adapted to correlate PWV with systolic and diastolic amplitude ratios. The form in which the blood pressure data is provided may include, for example, a look-up table, a spreadsheet, a graph, an equation correlating the PWV with the amplitude ratios or a database.

At step 408, the PWV value calculated at step 404 is compared with previously acquired blood pressure data of step 406 in order to obtain optimal systolic and diastolic ratios. According to an illustrative embodiment wherein the blood pressure data is complied in the form of a look-up table (not shown), the optimal systolic and diastolic ratios are obtainable by indexing the previously acquired systolic and diastolic ratios that most closely corresponds to the PWV value calculated at step 404. At step 410 the optimal systolic and diastolic ratios are used to recalculate SBP and DBP in a manner similar to that previously described with respect to step 208 of the algorithm 200 (shown in FIG. 4). The recalculated SBP and DBP values are generally more accurate than conventional SBP/DBP estimates because the recalculated values are based on optimal systolic and diastolic amplitude ratios selected to compensate for the effects of arterial compliance.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A method for estimating systolic blood pressure and diastolic blood pressure comprising:
   obtaining a pulse transit time slope from a patient;
   providing previously acquired blood pressure data obtained from a plurality of different subjects to a processor, said previously acquired blood pressure data adapted to convey the manner in which a systolic amplitude ratio and a diastolic amplitude ratio vary with respect to the pulse transit time slope obtained from the patient;
   implementing the previously acquired blood pressure data in the processor to select a systolic amplitude ratio and a diastolic amplitude ratio that most closely correlate with the pulse transit time slope obtained from the patient, wherein the selected systolic amplitude ratio and diastolic amplitude ratio are adapted to compensate for the effects of arterial compliance;
   implementing the selected systolic amplitude ratio in the processor to estimate a systolic blood pressure level; and
   implementing the selected diastolic amplitude ratio in the processor to estimate a diastolic blood pressure level.

2. The method of claim 1, wherein said obtaining a predetermined type of blood pressure data includes implementing a non-invasive blood pressure monitor and a pulse oximeter device.

3. The method of claim 1, wherein said obtaining the pulse transit time slope includes obtaining at least two pulse transit times from the patient.

4. The method of claim 1, wherein said providing previously acquired blood pressure data obtained from the plurality of different subjects includes providing the previously acquired blood pressure data in the form of an equation.

5. The method of claim 1, wherein said providing previously acquired blood pressure data obtained from the plurality of different subjects includes providing the previously acquired blood pressure data in the form of a table.

6. A method for estimating systolic blood pressure and diastolic blood pressure comprising:
   providing a non-invasive blood pressure monitor comprising a cuff configured to apply a selectable pressure level to a patient;
   estimating a first pulse transit time in a processor at a first cuff pressure level, and estimating a second pulse transit time in the processor at a second cuff pressure level;
   calculating a pulse transit time ratio in the processor defined as the first pulse transit time divided by the second pulse transit time;
   providing blood pressure data in the processor adapted to correlate a plurality of pulse transit time ratios with a plurality of systolic amplitude ratios and a plurality of diastolic amplitude ratios;
   selecting one of the plurality of systolic amplitude ratios and one of the plurality of diastolic amplitude ratios that most closely correlate with the calculated pulse transit time ratio, wherein the selected systolic amplitude ratio and the selected diastolic amplitude ratio are adapted to compensate for the effects of arterial compliance;

implementing the selected systolic amplitude ratio in the processor to estimate a systolic blood pressure level; and implementing the selected diastolic amplitude ratio in the processor to estimate a diastolic blood pressure level.

7. The method of claim 6, further comprising providing a pulse oximeter device operatively configured for connection to a patient.

8. The method of claim 7, wherein said estimating a first pulse transit time comprises:

identifying a pulse at a first location within the patient using the non-invasive blood pressure monitor;

identifying said pulse at a second location within the patient using the pulse oximeter device; and measuring the elapsed time between the identification of the pulse at the first location and the identification of the pulse at the second location.

9. The method of claim 6, wherein said providing blood pressure data includes providing multiple blood pressure measurements taken from a plurality of different subjects.

10. The method of claim 9, wherein said providing blood pressure data includes providing blood pressure data acquired with an intra-arterial procedure, an auscultatory procedure, and/or an oscillometric procedure.

11. The method of claim 9, wherein said providing blood pressure data includes providing the blood pressure data in the form of an equation.

12. The method of claim 9, wherein said providing blood pressure data includes providing the blood pressure data in the form of a table.

13. A method for estimating systolic blood pressure and diastolic blood pressure comprising:

estimating a pulse wave velocity in a processor of a pulse being transmitted through a patient;

providing blood pressure data in the processor adapted to correlate a plurality of pulse wave velocity values with a plurality of systolic amplitude ratios and a plurality of diastolic amplitude ratios;

selecting one of the plurality of systolic amplitude ratios and one of the plurality of diastolic amplitude ratios that are most closely correlated with the estimated pulse wave velocity, wherein the selected systolic amplitude ratio and the selected diastolic amplitude ratio are adapted to compensate for the effects of arterial compliance;

implementing the selected systolic amplitude ratio in the processor to estimate a systolic blood pressure level; and implementing the selected diastolic amplitude ratio in the processor to estimate a diastolic blood pressure level.

14. The method of claim 13, wherein said estimating a pulse wave velocity includes implementing a non-invasive blood pressure monitor and pulse oximeter device to estimate the pulse wave velocity.

15. The method of claim 14, wherein said estimating a pulse wave velocity includes:

identifying the pulse at a first location within the patient using the non-invasive blood pressure monitor;

identifying the pulse at a second location within the patient using the pulse oximeter device;

estimating the distance between the first location and the second location;

estimating a pulse transit time comprising the time required for said pulse to travel from the first location and the second location; and dividing the distance by the pulse transit time.

16. The method of claim 13, wherein said providing blood pressure data includes providing multiple blood pressure measurements taken from a plurality of different subjects.

17. The method of claim 16, wherein said providing blood pressure data includes providing blood pressure data acquired with an intra-arterial procedure, an auscultatory procedure, and/or an oscillometric procedure.

18. The method of claim 16, wherein said providing blood pressure data includes providing the blood pressure data in the form of an equation.

19. The method of claim 16, wherein said providing blood pressure data includes providing the blood pressure data in the form of a table.

* * * * *